US005358501A

United States Patent [19]

Meyer

[11] Patent Number: 5,358,501

[45] Date of Patent: Oct. 25, 1994

[54] STORAGE BOTTLE CONTAINING A CONSTITUENT OF A MEDICINAL SOLUTION

[75] Inventor: Gabriel Meyer, Vesenaz, Switzerland

[73] Assignee: Becton Dickinson France S.A., Pont de Claix, France

[21] Appl. No.: 140,717

[22] PCT Filed: Nov. 10, 1990

[86] PCT No.: PCT/EP90/01884

§ 371 Date: Jul. 11, 1991

§ 102(e) Date: Jul. 11, 1991

[87] PCT Pub. No.: WO91/07160

PCT Pub. Date: May 30, 1991

Related U.S. Application Data

[63] Continuation of Ser. No. 721,584, Jul. 11, 1991, abandoned.

[30] Foreign Application Priority Data

Nov. 13, 1989 [CH] Switzerland .................... 04081/89-4

[51] Int. Cl.[5] .............................................. A61B 19/00

[52] U.S. Cl. .................................... 604/414; 604/415; 604/412; 604/411; 604/403

[58] Field of Search ............... 604/403, 404, 405, 406, 604/408, 410, 411, 412, 413, 414

[56] References Cited

U.S. PATENT DOCUMENTS

| | | | |
|---|---|---|---|
| Re. 29,656 | 6/1978 | Crittenden et al. | 604/413 |
| 3,033,202 | 5/1962 | Richter et al. | 604/414 |
| 3,674,028 | 7/1972 | Ogle . | |
| 3,739,779 | 6/1973 | Pfleger | 604/411 X |
| 3,857,392 | 12/1974 | Ogle | 604/414 X |
| 3,858,580 | 1/1975 | Ogle | 604/414 X |
| 3,977,555 | 8/1976 | Larson | 604/411 X |
| 4,381,776 | 5/1983 | Latham, Jr. | 604/408 X |
| 4,543,101 | 9/1985 | Crouch | 604/411 |
| 4,610,374 | 9/1986 | Buehler | 604/412 X |
| 4,865,189 | 9/1989 | Guerra et al. . | |

FOREIGN PATENT DOCUMENTS

| | | | |
|---|---|---|---|
| 8900836 | 2/1989 | PCT Int'l Appl. . | |
| 528471 | 10/1940 | United Kingdom | 604/412 |

*Primary Examiner*—Robert A. Hafer
*Assistant Examiner*—Sam Rimell

[57] ABSTRACT

The storage bottle (10) contains a component of a medicinal solution (13) and a transfer device (11) for transferring it, after mixture with a solvent, into a container for final use. This bottle comprises a narrow neck (12) in which there engages, during the storage phase, a sealing element (15) composed of two elements: a first element **(16*a*) consisting of a solid elastomeric plug and a second element (16*b*)** consisting of an elastomeric toric connection. One opening at least empties into the space formed between the first and the second element of the sealing means.

6 Claims, 14 Drawing Sheets

STORAGE BOTTLE CONTAINING A CONSTITUENT OF A MEDICINAL SOLUTION

This is a continuation of copending application Ser. No. 07/721,584 filed on Jul. 11, 1991 abandoned.

The present invention concerns a storage bottle containing a component of a medicinal substance and a transfer device for transferring said substance either directly, or after mixing it with another substance, into a container for final use, said bottle comprising a narrow open neck and the transfer device comprising a sealing means at least partially engaged in said neck, at least during storage.

Medicinal substances, whether usable directly or comprising the components of a mixture, are usually stored in receptacles which may be either flame sealed glass ampoules or bottles sealed with a sealing means. In the case where the substance is obtained by dissolving a powder or a lyophilisate using a liquid solvent, this liquid must be introduced into the storage bottle to come into contact with the solid or pulverized component and dissolve it. To do this, the sealing means must be punctured for the liquid to flow through, or pushed back completely inside the bottle so as to free the neck, or even partially pushed back so as to free a lateral opening allowing the liquid to pass through.

A first problem posed by bottles known in the art is that which arises when the sealing means is punctured to pour the solvent inside the bottle. Puncturing it may break off some elastomeric material from the plug usually used as a sealing means, and the broken particles may in some cases be injected into the organism and cause serious problems.

The present invention remedies the disadvantages of known prior art systems and eliminates all the risks connected with puncturing the plug.

A second problem posed by bottles known in the art is that of the sealing barrier and the aseptic barrier. The sealing means must fulfill several functions and must respond to several requirements at the same time during storage and during use.

During storage, it must constitute both a tight barrier and an aseptic barrier especially for preventing any bacteria from entering the bottle. During the phase of use, the sealing means must maintain, particularly in the initial phase of activation, an aseptic barrier to protect the bottle contents and to allow access inside the bottle for the solvent to penetrate it.

The present invention is designed to resolve this problem by structuring the sealing means in such a way that it can fulfill all the functions described above.

A third problem posed by bottles known in the art is due to the fact that when the component is dissolved by the solvent, large quantities of gas may be discharged, particularly anhydrous carbon, which causes considerable pressure in the bottle or in the container for use. In the case where the container for use has a large capacity or when it is rigid and its walls resist pressure, the gas may be transferred into this container. On the other hand, when the container is a flexible pouch and when too great a pressure would risk causing it to burst, it is imperative that this gas be at least partially evacuated.

The present invention also overcomes this problem by providing means for evacuating the pressurized gas inside the storage bottle at the time the solvent dissolves the pulverized solid substance.

These various objectives are attained either separately or in combination by virtue of the bottle according to the invention.

To this end, the bottle is characterized in that the sealing means consists of two elements: a first element consisting of a solid elastomeric plug with a diameter essentially equal to that of the bottle neck and which is engaged in the neck to seal it tightly during storage, and a second element consisting of an elastomeric toric connection with an outside diameter essentially equal to that of the bottle neck and which engages in the neck, and in that the transfer device further comprises at least one inside opening emptying into the space formed between said first element and said second element.

According to an advantageous embodiment, the transfer device comprises a capsule adapted above the bottle neck, movable between a storage position in which it is partially engaged on the neck and an activated position in which it is completely engaged on the neck, and the capsule is integral with the sealing means.

Said first element of the sealing means is preferably independent and designed to detach and fall inside the bottle during the usage phase.

According to another embodiment said first element of the sealing means may be connected to the capsule.

Advantageously, said first element is a lyophilisation plug consisting of a solid upper portion and a lower extension provided with lateral vent holes, said extension being designed to allow the plug to be prepositioned on the bottle neck during lyophilisation of the substance contained in the bottle.

In the preferred embodiment of the device, the capsule comprises a generally cylindrical inside portion comprising at least one shoulder serving to contact said second element of the sealing means and provided with at least one opening emptying into the space defined by the two elements and by the inside surface of the neck in the storage position of the bottle.

Said second opening emptying into the space formed between said first and second elements may be disposed in the wall of the central portion of the capsule and may allow communication between said space and a central cavity of said capsule.

According to a particularly advantageous embodiment, the transfer device is provided with a least one vent hole also opening into the space formed between said first element and said second element of the sealing means. Said vent hole may comprise a calibrated orifice and may be associated with a filter.

Preferably said filter is of the hydroponic type.

According to another advantageous embodiment, said vent hole may consist of a second conduit of a dual-conduit trocar, the openings of said second conduit being spaced apart in relation to those of said first conduit.

Said vent hole may also be formed in the base of the central portion of the capsule and may open into the central cavity of said capsule.

The invention will be better understood with reference to the description of some exemplary embodiments and to the attached drawing, in which.

Figure 1:
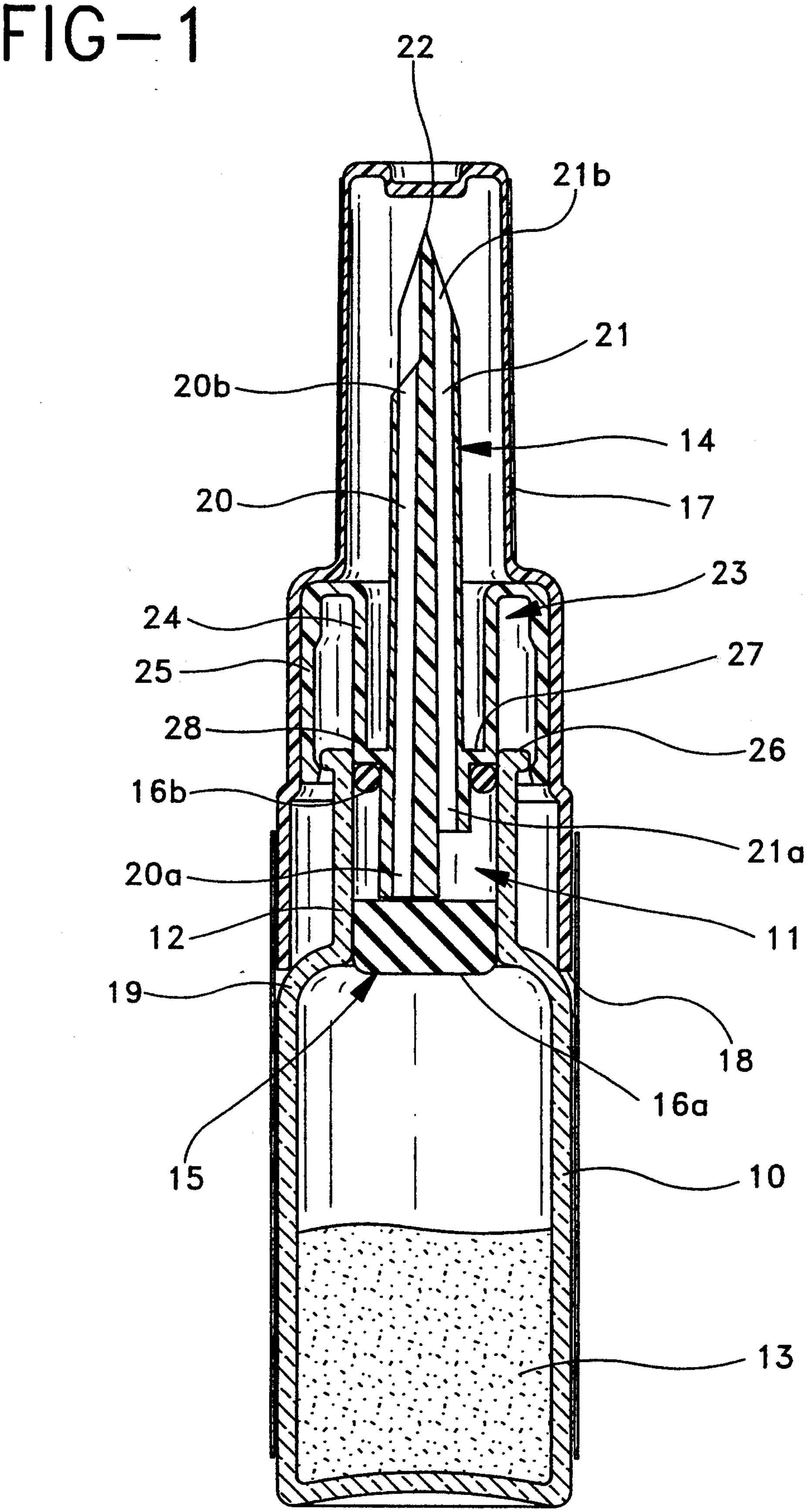
FIGS. 1, 2 and 3 illustrate a first embodiment of the bottle according to the invention containing a powdered substance, successively during the storage phase, the phase of solvent transfer and the phase of transferring the final solution of medicinal substance.
Figure 2:
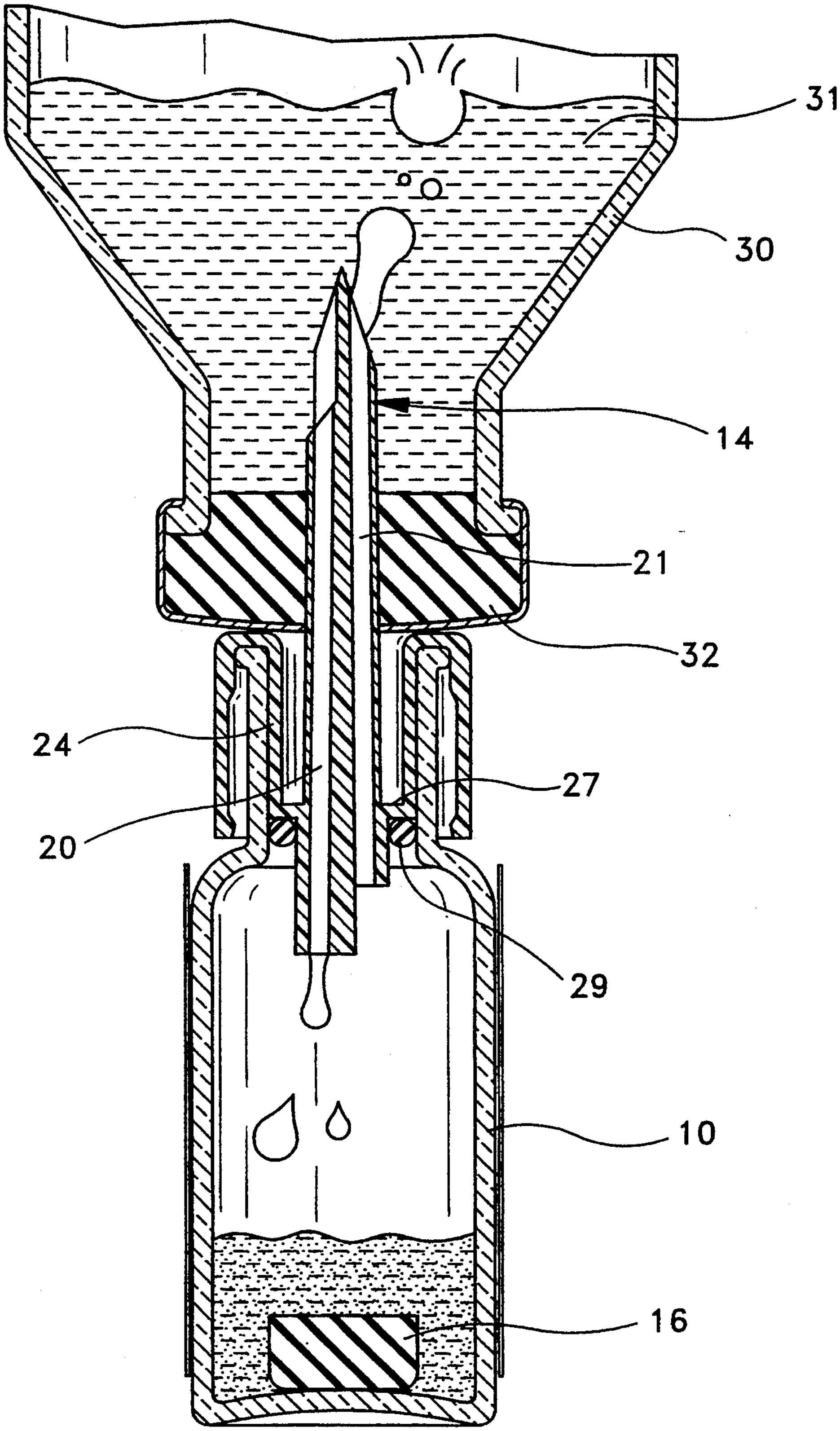
Figure 3:
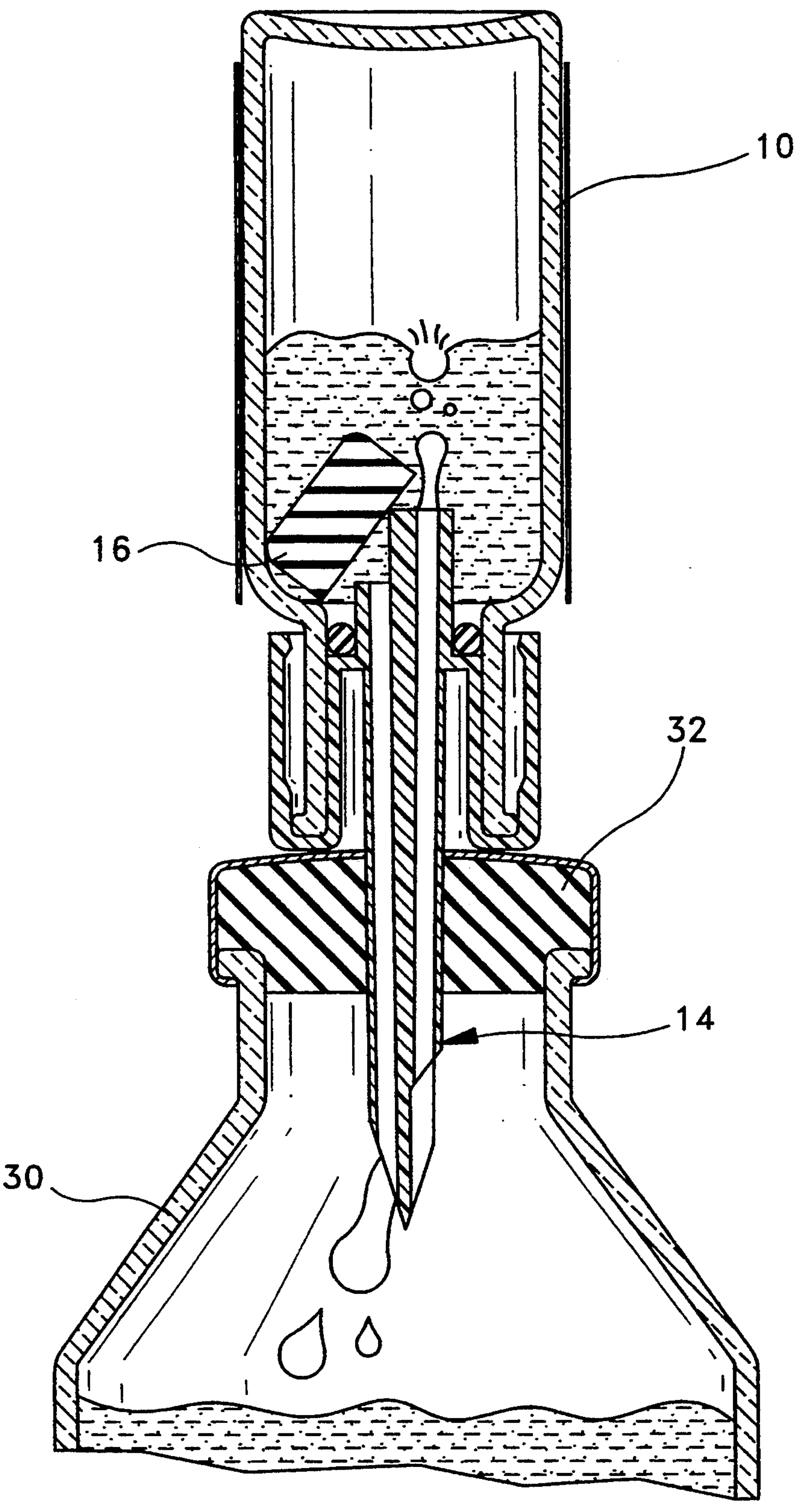

With reference to FIGS. 1 through 3, storage bottle 10 is associated with a transfer device 11 adapted on neck 12 of bottle 10 containing a medicinal substance 13 in powdered state. Neck 12 of bottle 10 is generally cylindrical and of reduced section in relation to that of the body.

Transfer device 11 consists in this case of an elongate element 14 in the form of a trocar consisting of a double needle and a sealing means 15. This sealing means comprises a first element consisting of a solid elastomeric plug 16*a* which is engaged in the neck and has a slightly greater diameter than the neck, and of a second element 16*b* also engaged in the neck and which consists of a toric elastomeric connection. This device is protected by a cap 17 covering the entire device and whose lower free rim 18 contacts a shoulder 19 which ensures the connection between the neck and the body of bottle 10. Elongate element 14 comprises two axial conduits, 20 and 21 respectively, each provided with a first orifice 20*a*, 21*a* respectively, designed to open inside the bottle, and with a second orifice 20*b*, 21*b* respectively, opening outside the bottle. Elongate element 14 ends in a point 22 at the end which is outside the bottle. Note that the orifices opening inside the bottle, that is, orifices 20*a* and 21*a*, are axially spaced apart from each other, and that orifices 20*b* and 21*b* opening outside the bottle are also axially spaced apart from each other.

A capsule 23 integral with sealing means 15 is engaged above bottle neck 12 and serves as a seat for cap 17. In the example shown, this capsule is integral with elongate element 14. It further serves as a support for second element 16*b* of sealing means 15.

In the position shown in FIG. 1, actually the storage position, bottle 10 is tightly sealed. The solid plug 16*a* constitutes a barrier tightly closing the bottle during storage. Capsule 23 comprises an interior portion 24, generally cylindrical and concave in shape, disposed to slide inside neck 12 of the bottle, and an exterior portion 25 passing above rim 26 of said neck 12, specifically at the moment when the device is moved from the storage position to the active position. The annular portion 27, which forms the connection between the inside portion 24 and the outside portion 25, defines a shoulder 28 beneath which there is a toric connection 29 which constitutes the second element 16*b* of the sealing means and which contacts the interior wall of bottle 12 to form an aseptic barrier during storage and a sealed connection and an aseptic barrier during the activation phase.

This phase is shown specifically in FIG. 2. Protective cap 17 has been withdrawn and the elongate element has been pushed inside a receptacle 30 containing a liquid 31 for dissolving powder 13 held in bottle 10. To do this, the elongate element has been used to puncture sealing plug 32 of receptacle 30. Then capsule 23 has been pushed down onto neck 12 of bottle 10, the effect of which is to push first element 16*a* of sealing means 15 inside the bottle and free openings 20*a* and 21*a*.

Because the orifices are spaced apart, liquid 31 held in receptacle 30 flows through axial conduit 20 inside bottle 10 and the air initially contained in bottle 10 or the gases generated by the reaction of solvent 31 on powder 13 are evacuated through axial passageway 21 in receptacle 30. In the case where the powder is a substance which reacts with the solvent by discharging a large quantity of gas, it is imperative that the receptacle be made of glass or a material resistant to elevated pressure. Liquid 31 dissolves powdered substance 13 and forms a liquid medicinal solution which may then be quasi-integrally transferred into receptacle 30 after turning over the unit as shown in FIG. 3.

Note that the transfer device allows two rigid bottles to be connected and that the transfer operation itself can take place in a sterile environment with minimal risk of contamination. The device allows pouring of any liquid substance to take place in two directions, that is from one bottle to another or reciprocally. Activation of the device is accomplished simply by sliding the transfer device associated with one of the bottles. The process may be interrupted at any time.

Figure 4:
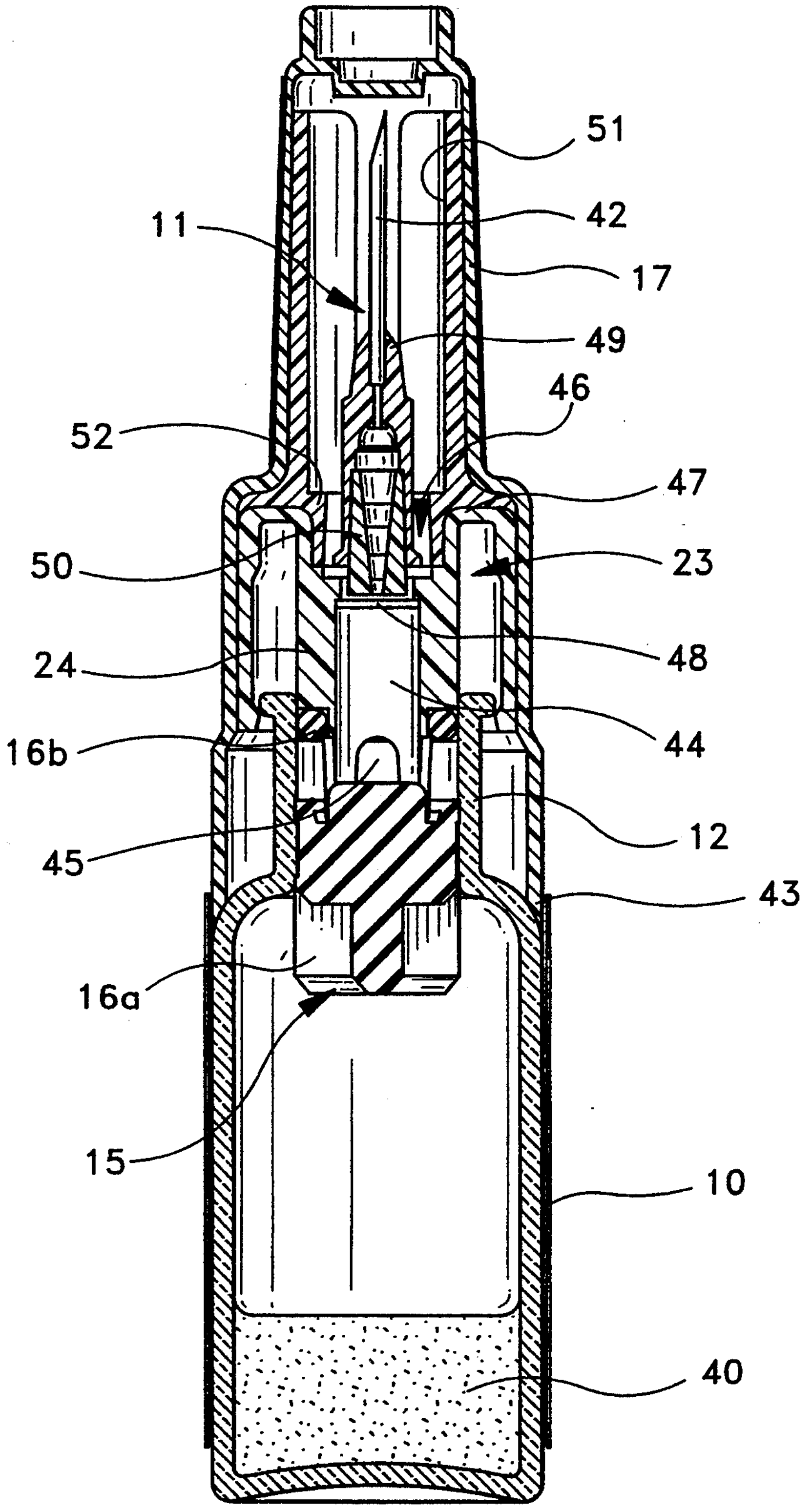
FIG. 4 shows a storage bottle according to the invention containing a lyophilisate, provided with an appropriate sealing plug.
Figure 5:
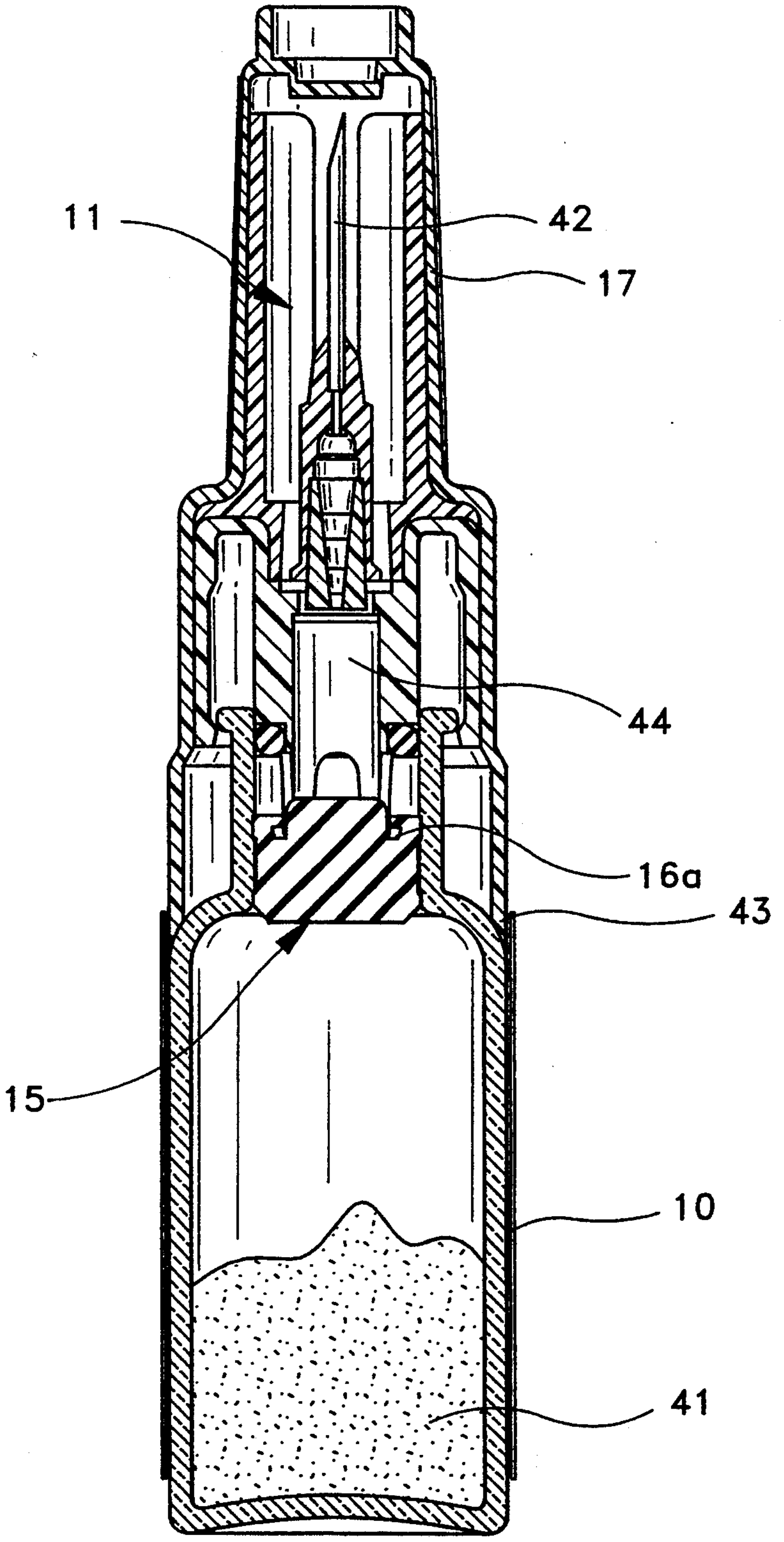
FIG. 5 shows the storage bottle of FIG. 4, containing a powder and provided with an appropriate sealing plug.

FIGS. 4 and 5 show two storage bottles which differ essentially by the fact that the first is designed to hold a lyophilisate 40 and the second a powder 41. This difference in use entails a difference in construction: the first bottle comprises a sealing means 15, the first element 16*a* of which is a lyophilisation plug such as that shown in perspective in FIG. 6, and the second bottle comprises a sealing means 15 of which the first element 16*a* is a simple plug such as that shown in perspective in FIG. 7.

In these two embodiments transfer device 11 consists of a needle 42 and a sealing means 15. It is, as in the preceding embodiment, protected by cap 17. During storage, cap 17 is connected to bottle 10 by a tamper-proof seal 43.

Sealing means 15 consists of said first element 16*a* defined above and of the second element 16*b* which is again an elastomeric toric connection situated between the internal surface of neck 12 of the bottle and the interior portion 24 of capsule 23. This interior portion comprises a central cavity 44 and, in the region situated between the first element 16*a* and the second element 16*b* of sealing means 15, has wide openings 45. In this embodiment, the interior portion 24 of capsule 23 is connected to said first element 16*a* of the sealing means.

The purpose of this is to prevent this element from falling inside the bottle when the latter is activated.

Capsule base 46 is provided with vent holes 47 whose function will be explained hereinafter. A filter 48 is attached inside base 46 and constitutes an obligatory passageway between the inside of the bottle and the central passageway of needle 42. This needle is integral with a needle-holding tip 49 and is attached to a cone 50 integral with capsule base 46.

Needle 42 is protected by a tubular element 51, which engages by its annular base 52 of angled section on the extremity of capsule 23.

During activation, the user, having previously punctured a bottle or pouch containing a liquid solvent (not shown) with needle 42, pushes the capsule back so that it is entirely engaged in the bottle neck. The first element 16*a* of sealing means 15 penetrates completely inside the bottle without, however, falling inside the bottle, since it is retained by the end of the interior portion 24 of capsule 23. The liquid passes through the central passageway in the needle, the central cavity in the capsule, openings 45, and penetrates the bottle. Dissolving lyophilisate 40 or powder 41 may in certain cases cause a considerable amount of gas to be discharged, specifically anhydrous carbon, which can escape through wide openings 45 and vent holes 47 without disturbing the flow of liquid or causing excessive pressure within the bottle.

Figure 6:
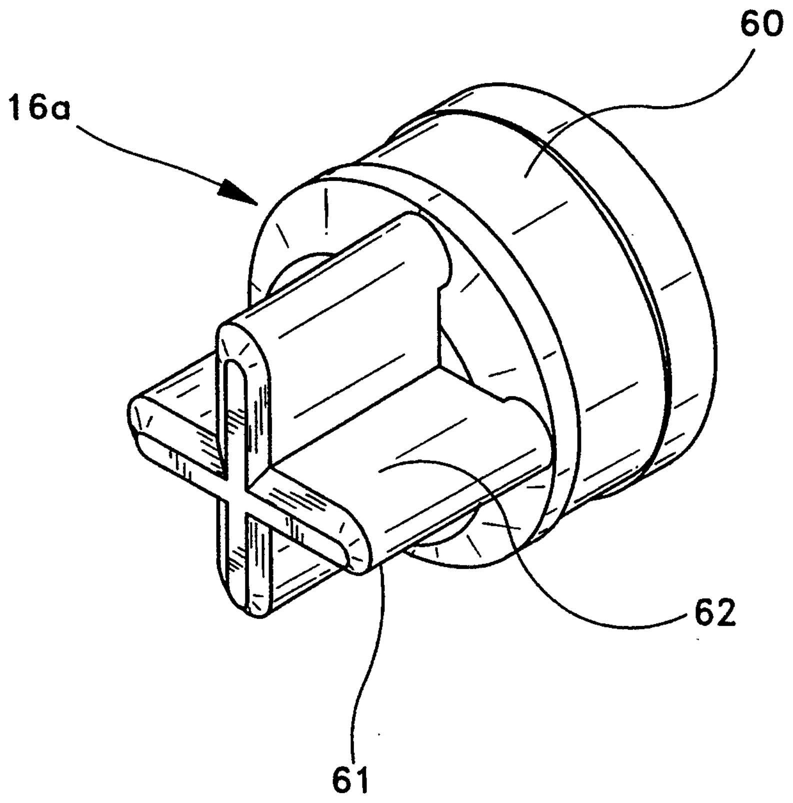
FIG. 6 shows a perspective view of the sealing plug of the storage bottle of FIG. 4.

Element 16*a* shown in FIG. 6 comprises a solid upper portion 60 and a tip 61 with a straight cross-shaped section forming lateral vent holes 62 for evacuating gases when element 16*a* is prepositioned on the bottle neck during the lyophilisation operation.

Figure 7:
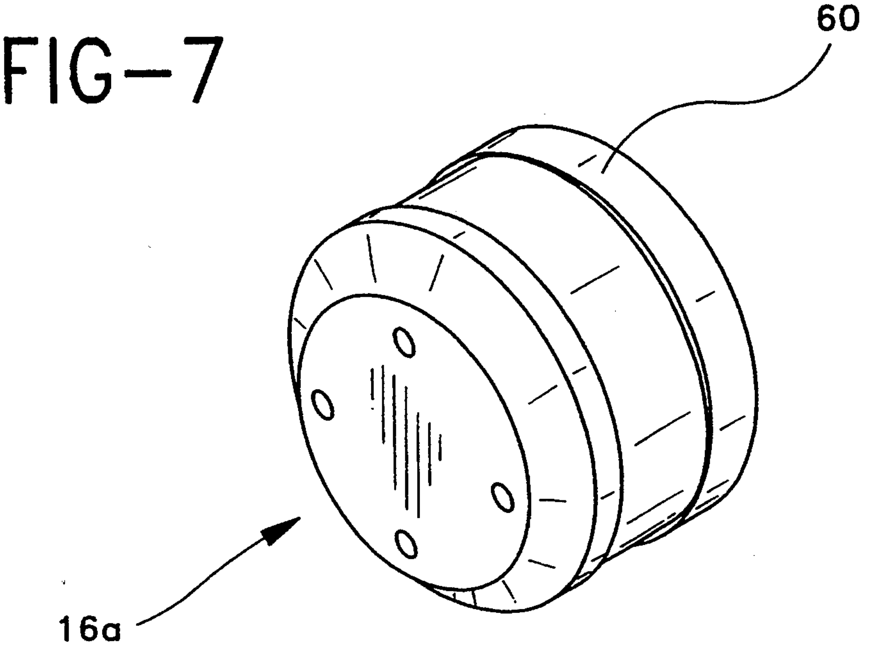
FIG. 7 shows a perspective view of the sealing plug of the storage bottle of FIG. 5.

Element 16*a* shown in FIG. 7 corresponds to the solid upper portion of the element shown in FIG. 6. When the bottle is filled with powder, the prepositioning tip necessary for lyophilsation may be eliminated.

Figure 8:
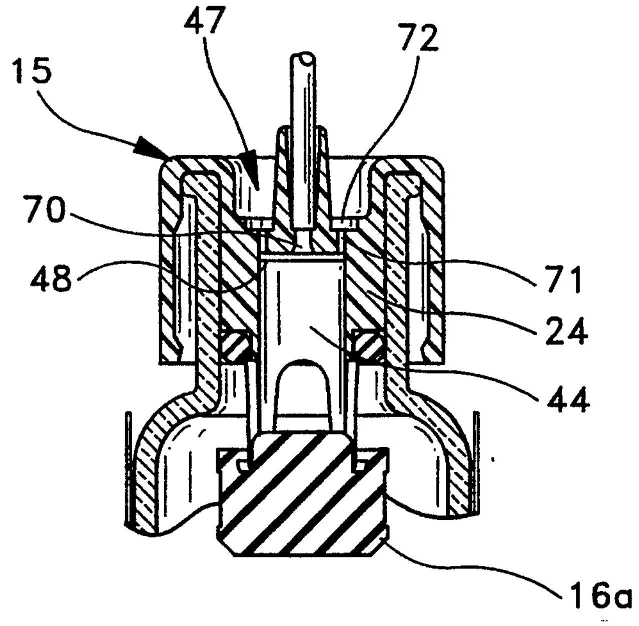
FIG. 8 shows a cross-section of one embodiment of the sealing means of a storage bottle according to the invention.
Figure 9:
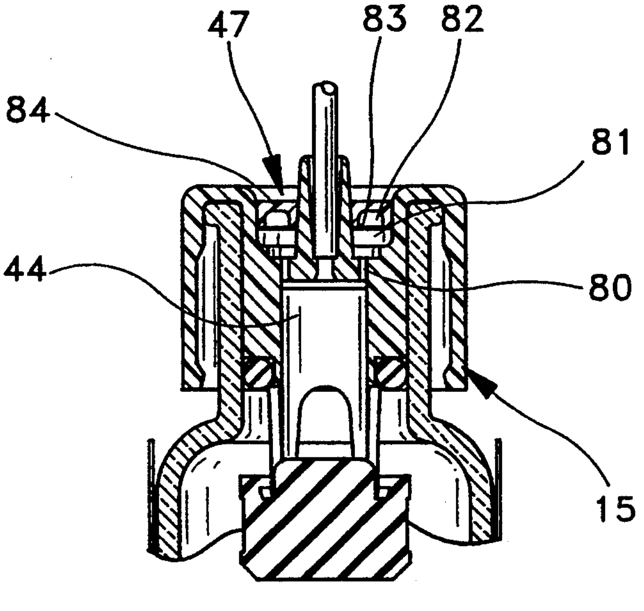
FIG. 9 shows a cross-section of another embodiment of the sealing means of a storage bottle according to the invention.

FIGS. 8 and 9 show two embodiments, seen in cross-section, of the sealing means of the bottle according to the invention. FIG. 8 shows a sealing means identical in every respect to that described above with reference to FIG. 5. However, the sealing means of FIG. 5 is shown in the storage position, while that of FIG. 8 is shown in the activated position. Notice in particular that the first element 16*a* of the sealing means is connected to the lower end of the interior portion 24 of capsule 23, thereby preventing this element from falling inside the bottle. In this embodiment, the base of central cavity 44 of the capsule is sealed by a filter 48. An opening 70 made in the base of this central cavity communicates via conduit 71 with an annular notch 72 to form the vent holes whose function has been described above.

The embodiment represented by FIG. 9 differs slightly in that vent holes 47 are designed differently. Central cavity 44 communicates via passageways 80 with an annular notch 81 which is separated from annular notch 82 by an annular filter 83 which is hydroponic. Notch 82 communicates with the outside by means of a passageway 84 which has a calibrated diameter. The diameter of this passageway is determined in such a way that the pressure which may be engendered by gas generation at the time the powder is dissolved by the solvent may be released slowly. Passageway 84 defines a measured release.

Figure 10:
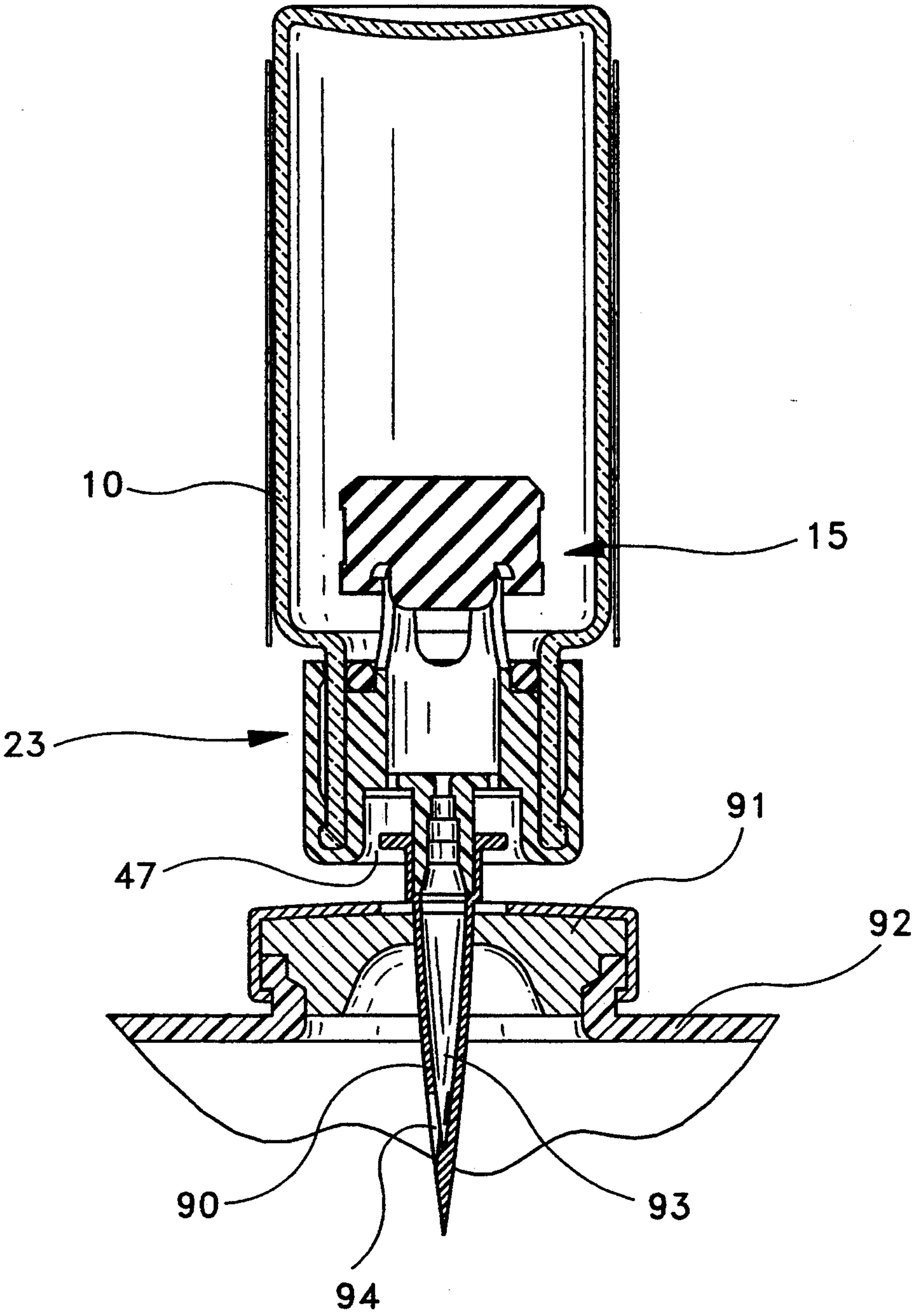
FIG. 10 shows a cross-section of a storage bottle according to the invention in the instance of a particular use.

FIG. 10 illustrates another use of the bottle according to the invention. Bottle 10, sealing means 15 and capsule 23 are in all respects identical to those described previously. The capsule is adapted to receive a needle 90 designed to puncture a plug 91 in a flexible bottle containing a liquid solvent. Needle 90 is preferably made of synthetic material and comprises a central passageway 93 and a lateral opening 94 for passage of the liquid for dissolving the medicinal substance initially held in the bottle, which is powdered or in the lyophilised state. As before, capsule 23 has vent holes 47 allowing the pressurized gases contained in the bottle to escape.

Figure 11:
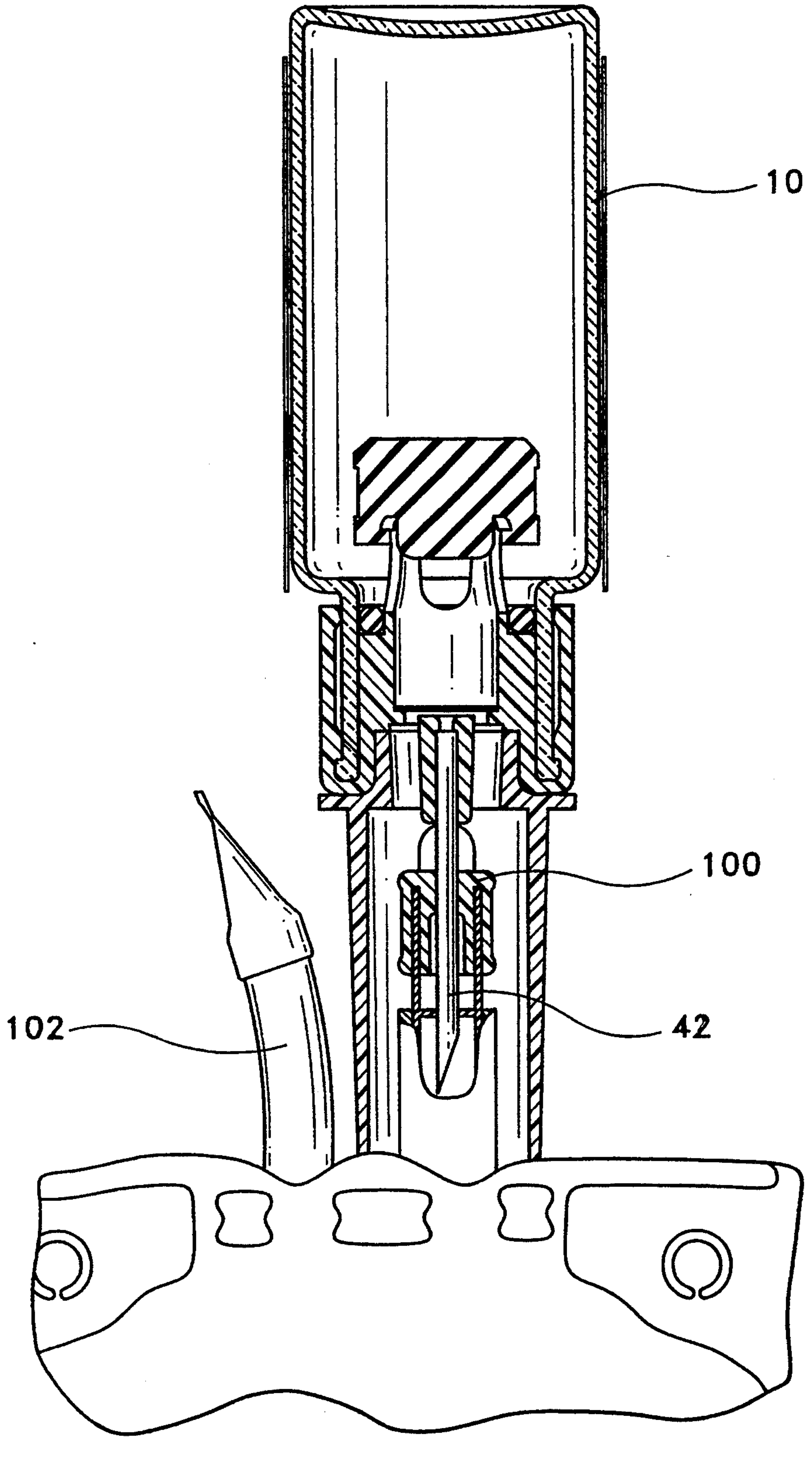
FIG. 11 shows a cross-section of a storage bottle according to the invention in the instance of another use.

FIG. 11 illustrates another use for the bottle according to the invention. This bottle is in every respect identical to that shown in FIG. 5. Needle 42 has punctured sealing plug 100 of a flexible transfusion pouch 101 with an intravenous device 102. This transfusion pouch contains the solvent which will be introduced into bottle 10 to dissolve the powder or the lyophilisate it contains before the solution is again poured into the transfusion pouch.

Figure 12:
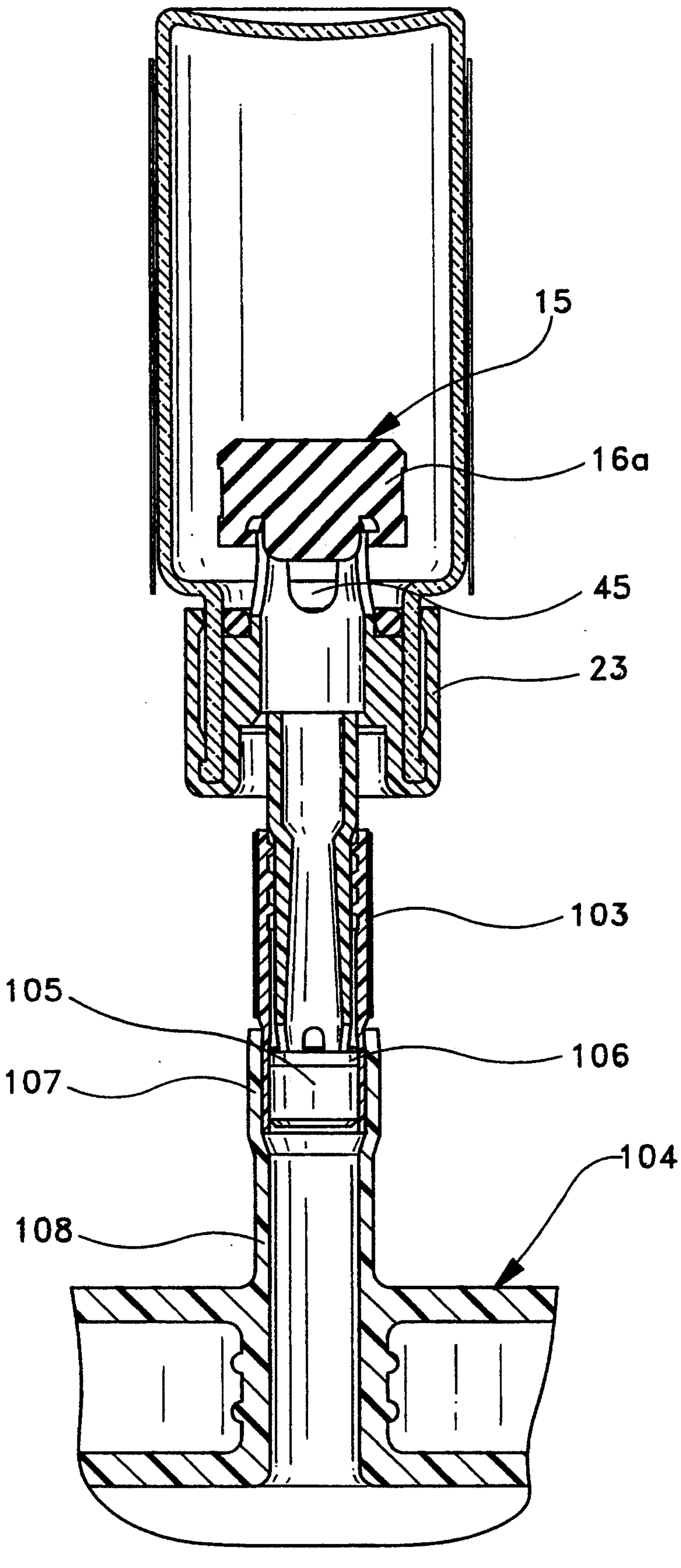
FIG. 12 shows a cross-section of a storage bottle according to the invention in the instance of a third use.

FIG. 12 illustrates an embodiment of the bottle in which capsule 23 is disposed to allow end tip 103 of a bottle 104 containing a liquid solvent to be screwed on. This end tip contains a plug 105 having an axial conduit 106 for the passage of the liquid in enlarged region 107 of neck 108 of bottle 104. The first element 16*a* of the sealing means 15 is attached to the end of capsule 23 which has at least one opening 45 for the passage of liquid.

Figure 13:
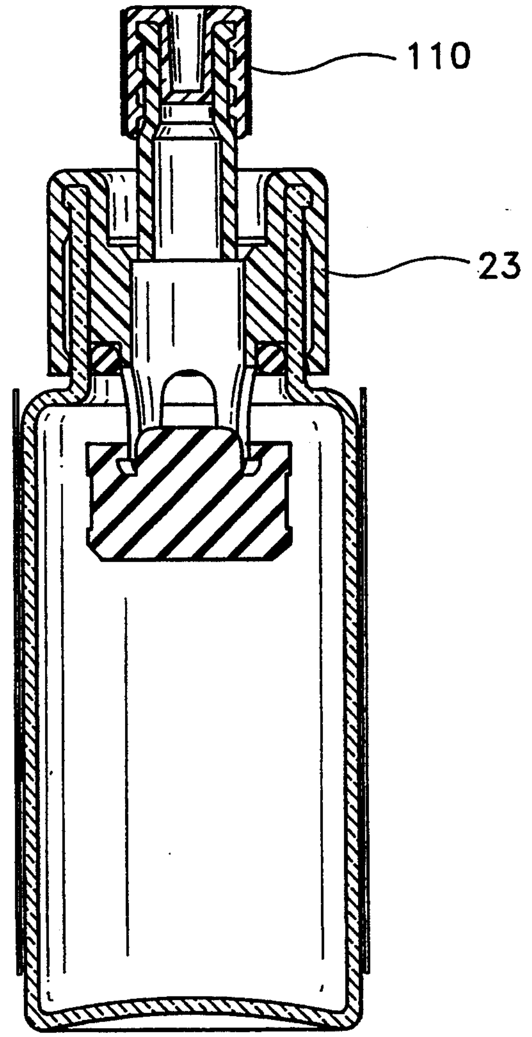
FIG. 13 shows a cross-section of a storage bottle according to the invention provided with a different transfer device.

FIG. 13 illustrates another embodiment in which capsule 23 is provided with a Luer-Lock type tip 110.

Figure 14:
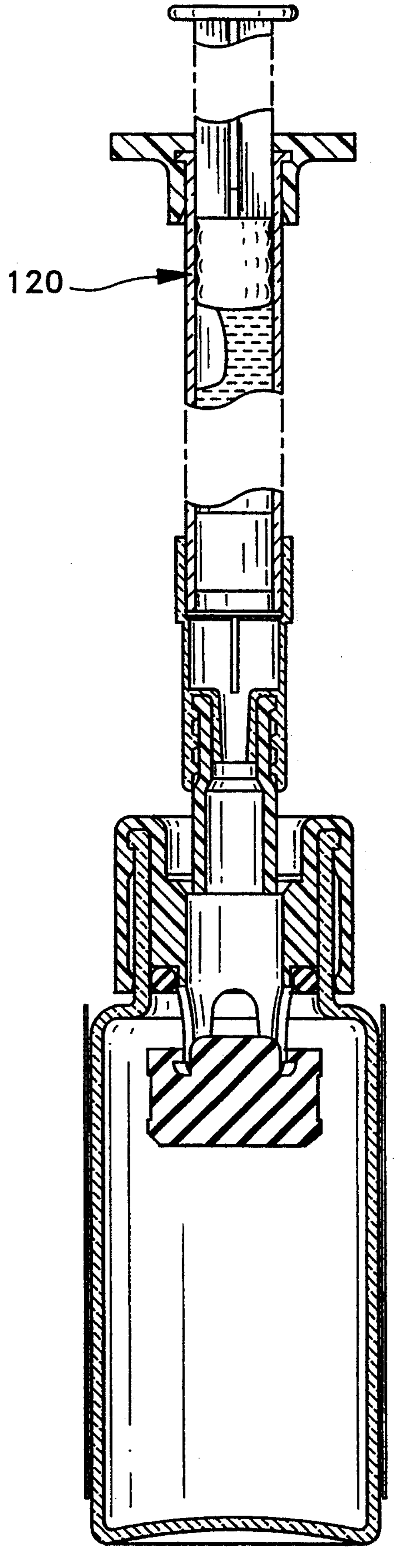
FIGS. 14 and 15 show two views of storage bottles associated with two distinct syringes.
Figure 15:
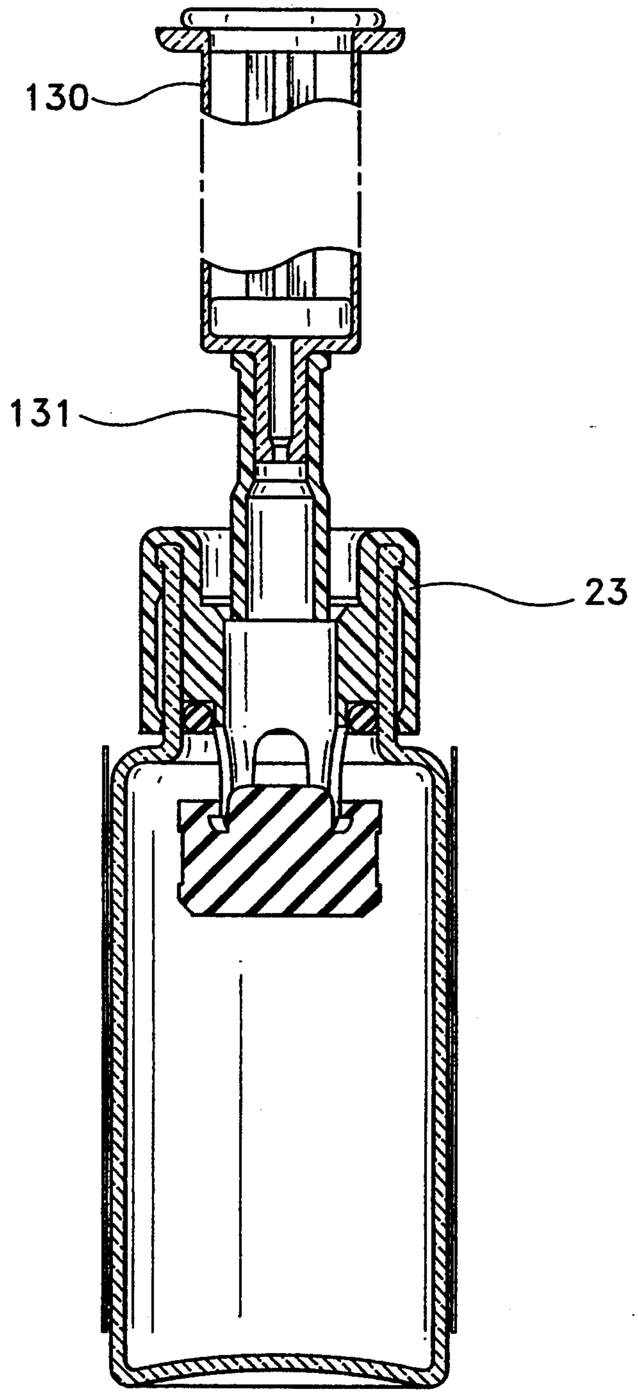

FIGS. 14 and 15 illustrate two uses of the bottle according to the invention when it is connected to syringes. In the example of FIG. 14, a pre-filled syringe 120 of known type is connected to a bottle having a capsule with a Luer-Lock type tip such as that shown in FIG. 13.

In the example of FIG. 15, a conventional syringe 130 is connected to a connecting tip 131 with a Luer cone integral with capsule 23.

Figure 16:
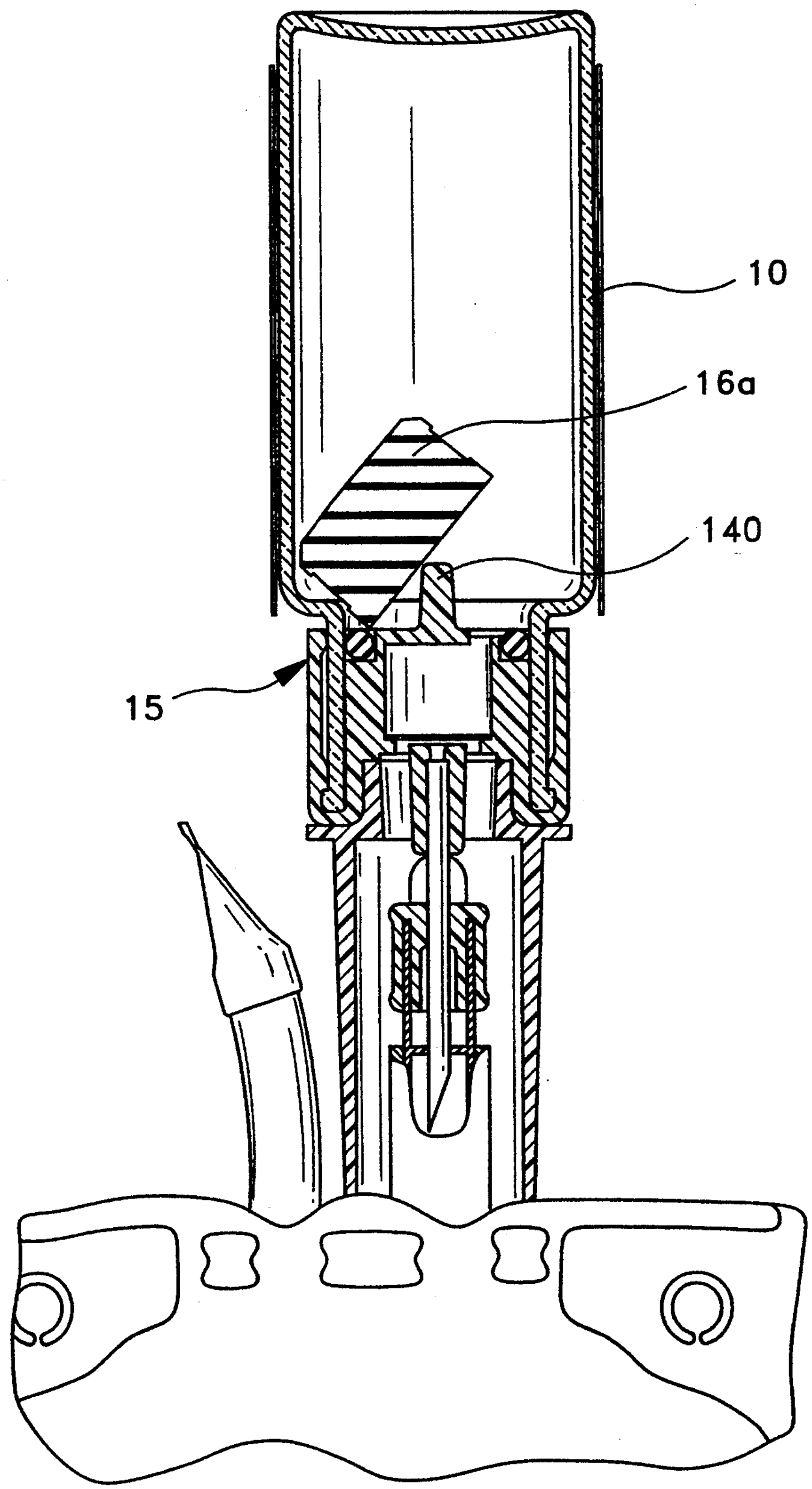
FIG. 16 shows a cross-section schematically illustrating another transfer device adapted on a storage bottle according to the invention.

The bottle illustrated in FIG. 16 has a capsule, that portion of the capsule oriented toward the inside of the bottle 10 extending into a projection 140 which serves as a button for pushing said first element 16*a* of sealing means 15 when the bottle is moved from the storage position to the activated position. In this case, said first element 16a of the sealing means 15 is not connected to the capsule as it was in most of the preceding embodiments.

It has been stated that in all of these embodiments the second element 16*b* of the sealing means has a dual function. During storage, this element acts as a protective barrier against bacteria and prevents contamination of the substance stored inside the bottle. During use, the second element constitutes a sealed connection preventing unwanted flow of the medicinal substance between the capsule and the inside wall of the bottle.

The present invention is not limited to the embodiments described, but may undergo various modifications and assume various embodiments obvious to one skilled in the art.

I claim:

1. A bottle comprising:

a bottle body having a neck of reduced diameter, a capsule slidably mounted to the neck of the bottle, the capsule including first and second conduits, the first and second conduits each having a bottom opening designed to open inside the bottle, the first and second conduits each having a top opening designed to open outside the bottle, the bottom opening of one of said conduits being disposed below the bottom opening of the other conduit, the top opening of one of said conduits being disposed above the top opening of the other conduit, the outer surface of the first and second conduits and the inner surface of the neck of the bottle defining an annular passage;

a first seal slidably mounted within the annular passage and above said bottom openings, said capsule including means for engaging said first seal such that said first seal slides with respect to said neck upon movement of the capsule, and a second seal slidably mounted within the neck of the bottle and engaging said capsule, the second seal preventing communication of the bottom openings of the first and second conduits and the annular space with the bottle when the first and second conduits and the second seal are in a storage position.

2. A bottle according to claim 1, wherein the bottom opening of the first conduit is disposed below the bottom opening of the second conduit and the top opening of the second conduit is disposed above the top of the first conduit.

3. A bottle according to claim 1 wherein said first seal is an O-ring seal.

4. A bottle according to claim 1 wherein said second seal is designed to detach from the neck and fall inside the bottle body.

5. A bottle according to claim 1, wherein said second seal is connected to said capsule.

6. A bottle according to claim 1, wherein said second seal sealingly engages the capsule at an upper portion of the seal, thereby sealing the bottom opening of said first conduit.

* * * * *